United States Patent [19]

Schneider et al.

[11] Patent Number: 5,399,756
[45] Date of Patent: Mar. 21, 1995

[54] PROCESS FOR THE PRODUCTION OF LIQUID AMINE ADDUCTS OF FLUORINE-CONTAINING AMIDES

[75] Inventors: Wolfgang Schneider; Karlheinz Stachulla, both of Leverkusen; Klaus Pohmer, Köln; Rainer Weber, Odenthal; Ottfried Schlak, Köln; Hans-Heinrich Moretto, Leverkusen, all of Germany

[73] Assignee: Bayer AG, Leverkusen, Germany

[21] Appl. No.: 276,423

[22] Filed: Jul. 18, 1994

[30] Foreign Application Priority Data

Jul. 29, 1993 [DE] Germany .................. 43 25 485.3

[51] Int. Cl.⁶ .................. C07C 303/38; C07C 303/40
[52] U.S. Cl. .................................................. 564/96
[58] Field of Search ............................................ 564/96

[56] References Cited

U.S. PATENT DOCUMENTS 4,370,254 1/1983 Mitschke et al. ............. 252/355

FOREIGN PATENT DOCUMENTS 0744213 6/1970 Belgium ........................ 564/96

OTHER PUBLICATIONS

Gramstad & Haszeldine, *Perfluoroalkyl Derivatives of Sulphur. Part VI. Perfluoroalkanesulphonic Acids*, J. Chem. Soc. pp. 2640–2645 (1957).

Primary Examiner—Peter O'Sullivan
Attorney, Agent, or Firm—Connolly & Hutz

[57] ABSTRACT

The invention relates to an improved process for the production of liquid amine adducts of fluorine-containing amides, in which the compounds are synthesized in the absence of solvents in two process steps without the synthesis of intermediate products.

16 Claims, No Drawings

PROCESS FOR THE PRODUCTION OF LIQUID AMINE ADDUCTS OF FLUORINE-CONTAINING AMIDES

This invention relates to an improved process for the production of liquid amine adducts of fluorine-containing amides, in which the compounds are synthesized in the absence of solvents in two process steps without the synthesis of intermediate products.

By virtue of their high interfacial activity, liquid amine adducts of fluorine-containing amides are used for various industrial applications. Typical applications include their use as polymerization emulsifiers, as flow control agents and wetting agents in photography and film manufacture, as flow control agents and wetting agents in water-dilutable lacquers (EP-B 0 021 003), or as a spreading agent in fire extinguishing foams.

Examples of such compounds are $C_8F_{17}SO_2NH_2 \cdot N(CH_3)_3$ and $C_4F_9SO_2NH_2 \cdot N(C_2H_5)_3$ According to EP-B 0 021 003, amine adducts are produced by reaction of perfluoroalkyl sulfonamides with tertiary amines in accordance with equation (1):

$$C_nF_{2n+1}SO_2NHR_H + N(R^1R^2R^3) \rightarrow C_nF_{2n+1}SO_2NHR_H \cdot N(R^1R^2R^3) \quad (1)$$

in which n is an integer of 4 to 20, $R^1$, $R^2$ and $R^3$ independently of one another represent a hydrogen atom, an alkyl, hydroxyalkyl or alkoxyalkyl radical containing 1 to 4 carbon atoms and $R_H$ is a hydrogen atom, an alkyl, hydroxyalkyl or alkoxyalkyl radical containing 1 to 4 carbon atoms.

The perfluoroalkyl sulfonamide required for this reaction is obtained by reaction of perfluoroalkyl sulfonyl fluoride with ammonia using organic solvents, for example diisopropyl ether, in accordance with equation (2):

$$C_nF_{2n+1}SO_2F + 2\,NH_3 \xrightarrow{\text{Solvent}} C_nF_{2n+1}SO_2NH_2 + NH_4F \quad (2)$$

(see, for example, T. Granstad, R. N. Haszeldine, J. Chem. Soc. (1957) 2640–45). The solvent performs various functions in this reaction. For example, it serves as an extractant for removing the perfluoroalkyl sulfonamide from ammonium fluoride. The perfluoroalkyl sulfonamide dissolves in a suitable solvent whereas the ammonium fluoride formed at the same time does not and may be removed, for example, by filtration. The solvent may also serve as a carrier liquid for the ammonia which is present in gaseous form at the appropriate reaction temperature. Since perfluoroalkyl sulfonamides are solid at room temperature, the addition of a solvent enables the reaction to be carried out in liquid phase which affords considerable advantages from the point of view of process technology, including for example better mixing of the reaction mixture and hence better temperature control and, optionally, a faster reaction. If the solvent is selected so that it is immiscible with water, the organic phase may be purified by washing.

To isolate the sulfonamide, the solvent-containing mixture may be purified with aqueous sulfuric or hydrochloric acid and the aqueous salt-containing phase may be separated off. The solvent-containing phase has to be repeatedly washed with demineralized water. The solvent is then removed by distillation. A highly pure perfluoroalkyl sulfonamide is obtained.

Disadvantages of using solvents in the production of perfluoroalkyl sulfonamides are, for example, the clearly reduced volume/time yield and the potential dangers often arising out of these solvents, more particularly the possibility of peroxide formation in ethers. In addition, the washing of the product results in a significant accumulation of polluted waste water, besides which the solvent has to be worked up or destroyed.

The problem addressed by the present invention was to provide a safe, simple and inexpensive process for the production of liquid amine adducts of fluorine-containing amides which would not have any of the disadvantages mentioned above.

It has now surprisingly been found that liquid amine adducts of fluorine-containing amides can be obtained directly without the formation of intermediate products providing fluorine-containing sulfonic acid halides are stoichiometrically reacted with a tertiary amine and ammonia or a primary amine. After filtration under a pressure of 1 to 6 bar and at a temperature of 20° to 120° C., a highly pure product with a halide content of less than 0.1% is obtained in accordance with equation (3):

$$R_F-(CH_2)_n-SO_2-X + 2NH_2R_H + N(R^1R^2R^3) \rightarrow R_F-(CH_2)_n-SO_2-NHR_H \cdot N(R^1R^2R^3) + R_HNH_3X \quad (3)$$

in which $R_F$ is a perfluoroalkyl radical containing 3 to 10 carbon atoms or a fluoroalkyl radical containing 3 to 10 carbon atoms, n is an integer of 0 to 6, X is a halogen atom, $R_H$ is a hydrogen atom or a linear alkyl radical containing 1 to 4 carbon atoms, $R^1$, $R^2$ and $R^3$ independently of one another represent a linear alkyl radical containing 1 to 4 carbon atoms.

The present invention relates to a process for the production of liquid amine adducts of fluorine-containing amides corresponding to general formula (I):

$$R_F-(CH_2)_n-SO_2-NHR_H \cdot N(R^1R^2R^3) \quad (I)$$

in which $R_F$ is a perfluoroalkyl radical containing 3 to 10 carbon atoms or a fluoroalkyl radical containing 3 to 10 carbon atoms, n is an integer of 0 to 6, $R_H$ is a hydrogen atom or a linear alkyl radical containing 1 to 4 carbon atoms, $R^1$, $R^2$ and $R^3$ independently of one another represent a linear alkyl radical containing 1 to 4 carbon atoms, characterized in that a fluorine-containing sulfonic acid halide corresponding to general formula (II):

$$R_F-(CH_2)_n-SO_2-X \quad (II)$$

in which $R_F$ and n are as defined above and

X is a halogen atom, a tertiary amine N(R$^1$R$^2$R$^3$), where R$^1$, R$^2$ and R$^3$ are as defined above, and ammonia or a primary amine H$_2$NR$_H$, where R$_H$ is as defined above, are reacted simultaneously with one another and the product obtained is freed from ammonium halides precipitated by filtration under a pressure of 1 to 6 bar and at a temperature of 20° to 120° C.

A corresponding process for the production of liquid amine adducts of fluorine-containing amides, in which R$_F$ is a C$_{4-8}$ perfluoroalkyl radical, is particularly preferred.

Sulfonic acid halides with n=0 are preferably used.

Processes for the production of liquid amine adducts of fluorine-containing halides, in which a filter aid and/or crystallization auxiliary is/are added before filtration, are preferred.

Processes for the production of liquid amine adducts of fluorine-containing amides, in which silica derivatives and/or cellulose powders are added, are particularly preferred.

Processes for the production of liquid amine adducts, in which water is added in a quantity of 1 to 4% by weight, based on the weight of the product, before filtration, are preferred.

Processes in which water is added in a quantity of 1.5 to 2.5% by weight, based on the weight of the product, are particularly preferred.

The process according to the invention is carried out in the absence of a solvent.

The process according to the invention is illustrated by the following Examples.

EXAMPLES

Fluorine-containing sulfonic acid halide and tertiary amine are introduced into a reaction vessel, preferably at a temperature of −40° C. to +10° C., and ammonia or primary amine is subsequently introduced with vigorous stirring. Alternatively, tertiary amine and ammonia or primary amine are introduced first and fluorine-containing sulfonic acid amide is subsequently added. The reaction is exothermic and should be kept at max. +10° C. by cooling and gradual introduction of the reactants. A beige-colored liquid of amine adduct of the fluorine-containing amide and ammonium fluoride is formed.

The ammonium fluoride formed is insoluble in the reaction mixture. It accumulates in very fine-particle form. The ammonium fluoride is removed by filtration.

The advantages of the solventless process lie in greater safety, in an improved volume/time yield, in reduced wastewater pollution, in a considerable reduction in the manual work involved and in an improvement in the quality of the end product through minimal exposure to high temperatures. There is no solvent to be worked up or destroyed.

Example 1

200 g (0.30 mol) of perfluorooctyl sulfonyl fluoride with a purity of >98% and 40.4 g (0.4 mol) of triethylamine with a purity of >99% are introduced into a stirred three-necked flask. 18 g (1.06 mol) of gaseous ammonia are introduced with intensive stirring at a temperature of −5° C. to +10° C. 5% Kieselgur is added to the reaction mixture obtained which is then filtered in a pressure nutsche with filter (Seitz K 300 ®) at 50° C./3 bar.

| Yield | 133.5 g | (corresponding to 57% of the theoretical) |
| --- | --- | --- |
| Fluoride content | 0.01% | |
| Surface tension | 24.3 mN/m | (100 mg/l water at 20° C.) |

Example 2

200 g (0.39 mol) of perfluorooctyl sulfonyl fluoride with a purity of >98% and 40.4 g (0.4 mol) of triethylamine with a purity of >99% are introduced into a stirred three-necked flask. 18 g (1.06 mol) of gaseous ammonia are introduced with intensive stirring at a temperature of −5° C. to +10° C. 5% Cellulose powder is added to the reaction mixture obtained which is then filtered in a pressure nutsche with filter (Seitz K 300 ®) at 50° C./3 bar.

| Yield | 148 g | (corresponding to 63% of the theoretical) |
| --- | --- | --- |
| Fluoride content | 0.02% | |
| Surface tension | 24.5 mN/m | (100 mg/l water at 20° C.) |

Example 3

1340 g (2.6 mol) of perfluorooctyl sulfonyl fluoride with a purity of >98% and 70 g (0.22 mol) of perfluorobutyl sulfonyl fluoride with a purity of 95% and 300 g (2.97 mol) of triethylamine with a purity of >99% are introduced into a stirred three-necked flask. 130 g (7.64 mol) of gaseous ammonia are introduced with intensive stirring at a temperature of −10° C. to +10° C. 36 g (2 mol) of water are added to the reaction mixture obtained which, after a conditioning time of 18 hours, is filtered in a pressure nutsche with filter (Seitz K 300 ®) at 20° C./3 bar.

| Yield | 1471 g | (corresponding to 86% of the theoretical) |
| --- | --- | --- |
| Fluoride content | 0.08% | |
| Surface tension | 25.5 mN/m | (100 mg/l water at 20° C.) |

Example 4

1359 g (4.3 mol) of perfluorobutyl sulfonyl fluoride with a purity of 95% and 466 g (4.6 mol) of triethylamine with a purity of >99% are introduced into a stirred three-necked flask. 202 g (11.9 mol) of gaseous ammonia are introduced with intensive stirring at a temperature of −10° C. to +10° C. 40 g (2.2 mol) of water are added to the reaction mixture obtained which, after stirring for 24 to 36 hours, is filtered in a pressure nutsche with filter (Seitz K 300 ®) at 20° C./3 bar.

| Yield | 1520 g | (corresponding to 78% of the theoretical) |
| --- | --- | --- |
| Fluoride content | 0.08% | |
| Surface tension | 57.8 mN/m | (100 mg/l water at 20° C.) |

Example 5

1000 g (2.49 mol) of perfluorohexyl sulfonyl fluoride with a purity of >98% and 257.5 g (2.55 mol) of triethylamine with a purity of >99% are introduced into a stirred three-necked flask. 130 g (7.64 mol) of gaseous ammonia are introduced with intensive stirring at a temperature of −5° C. to +10° C. 36 g (2 mol) of water are added to the reaction mixture obtained which, after conditioning for 48 hours, is filtered in a pressure nutsche with filter (Seitz K 300 ®) at 20° C./3 bar.

| Yield | 1144 g | (corresponding to 93% of the theoretical) |
|---|---|---|
| Fluoride content | 0.09% | |
| Surface tension | 39.6 mN/m | (100 mg/l water at 20° C.) |

Comparison Example 400 g of $C_8F_{17}SO_2F$ in 800 ml of diisopropyl ether are initially introduced and cooled with stirring to 5° C. 55 g of $NH_3$ gas are introduced for about 1.3 h under a reduced pressure of about 500 mbar at such a rate that the sump temperature does not rise above 16° C. This is followed by stirring for about 1 hour at room temperature. 850 ml of 11% HCl are then added dropwise with stirring and cooling. After addition of the HCl, the reaction mixture is briefly heated to 45° C. and, after cooling, the phases are separated. The organic phase is washed with a solution of 17.5 g of iron(II) sulfate and 55 g of conc. HCl in 400 ml of water. The phases are then separated. The ether is distilled off from the organic phase. The residue remaining is dried. 111 ml of triethylamine are added with stirring over a period of about 45 minutes at 110 to 120° C., a thick mist initially being formed. After stirring for 10 minutes at 120 to 130° C., the reaction mixture is cooled to 40° C. The yield amounts to 422.9 g.

What is claimed is:

1. A process for the production of liquid amine adducts of fluorine-containing amides corresponding to general formula (I):

$$R_F-(CH_2)_n-SO_2-NHR_H\cdot N(R^1R^2R^3) \qquad (I)$$

in which
$R_F$ is a perfluoroalkyl radical containing 3 to 10 carbon atoms or a fluoroalkyl radical containing 3 to 10 carbon atoms,
n in an integer of 0 to 6,
$R_H$ is a hydrogen atom or a linear alkyl radical containing 1 to 4 carbon atoms,
$R^1$, $R^2$ and $R^3$ independently of one another represent a linear alkyl radical containing 1 to 4 carbon atoms,
characterized in that a fluorine-containing sulfonic acid halide corresponding to general formula (II):

$$R_F-(CH_2)_n-SO_2-X \qquad (II)$$

in which
$R_F$ and n are as defined above and
X is a halogen atom,
a tertiary amine $N(R^1R^2R^3)$, where $R^1$, $R^2$ and $R^3$ are as defined above, and ammonia or a primary amine $H_2NR_H$, where $R_H$ is as defined above, are reacted simultaneously with one another and the product obtained is freed from ammonium halides precipitated by filtration under a pressure of 1 to 6 bar and at a temperature of 20° to 120° C.

2. A process for the production of liquid amine adducts as claimed in claim 1, characterized in that $R_F$ is a perfluoroalkyl radical containing 4 to 8 carbon atoms.

3. A process for the production of liquid amine adducts as claimed in claim 1, characterized in that n=0.

4. A process for the production of liquid amine adducts as claimed in claim 1, characterized in that at least one of a filter aid and a crystallization auxiliary is added before filtration.

5. A process for the production of liquid amine adducts as claimed in claim 4, characterized in that at least one of silica derivatives and cellulose powder are added before filtration.

6. A process for the production of liquid amine adducts as claimed in claim 1, characterized in that water is added before filtration in a quantity of 1 to 4% by weight, based on the weight of the product.

7. A process for the production of liquid amine adducts as claimed in claim 6, characterized in that water is added in a quantity of 1.5 to 2.5% by weight, based on the weight of the product.

8. A process for the production of liquid amine adducts as claimed in claim 2, characterized in that n=0.

9. A process for the production of liquid amine adducts as claimed in claim 2, characterized in that at least one of a filter aid and a crystallization auxiliary is added before filtration.

10. A process for the production of liquid amine adducts as claimed in claim 3, characterized in that at least one of a filter aid and a crystallization auxiliary is added before filtration.

11. A process for the production of liquid amine adducts as claimed in claim 2, characterized in that water is added before filtration in a quantity of 1 to 4% by weight, based on the weight of the product.

12. A process for the production of liquid amine adducts as claimed in claim 3, characterized in that water is added before filtration in a quantity of 1 to 4% by weight, based on the weight of the product.

13. A process for the production of liquid amine adducts as claimed in claim 9, characterized in that at least one of silica derivatives and cellulose powder are added before filtration.

14. A process for the production of liquid amine adducts as claimed in claim 10, characterized in that at least one of silica derivatives and cellulose powder are added before filtration.

15. A process for the production of liquid amine adducts as claimed in claim 11, characterized in that water is added in a quantity of 1.5 to 2.5% by weight, based on the weight of the product.

16. A process for the production of liquid amine adducts as claimed in claim 12, characterized in that water is added in a quantity of 1.5 to 2.5% by weight, based on the weight of the product.

* * * * *